United States Patent [19]

Burton et al.

[11] Patent Number: 4,478,761

[45] Date of Patent: Oct. 23, 1984

[54] METHOD FOR PREPARING FLUORINE-CONTAINING PHOSPHONATES

[75] Inventors: Donald J. Burton, Iowa City, Iowa; Richard M. Flynn, Bethesda, Md.

[73] Assignee: University of Iowa Research Foundation, Iowa City, Iowa

[21] Appl. No.: 487,543

[22] Filed: Apr. 22, 1983

Related U.S. Application Data

[62] Division of Ser. No. 143,995, Apr. 28, 1980, Pat. No. 4,330,486.

[51] Int. Cl.$^3$ .............................................. C07F 9/40
[52] U.S. Cl. .................................... 260/970; 260/932
[58] Field of Search ........................................ 260/970

[56] References Cited

U.S. PATENT DOCUMENTS

| | | | |
|---|---|---|---|
| 2,599,761 | 6/1952 | Harman et al. | 252/49.9 |
| 2,634,288 | 4/1953 | Boyer et al. | 260/970 |
| 3,242,236 | 3/1966 | Moedritzer | 260/970 |
| 3,256,370 | 6/1966 | Fitch et al. | 260/97 |
| 3,404,178 | 10/1968 | Roy | 260/502.4 |
| 3,422,021 | 1/1969 | Roy | 252/161 |
| 3,471,552 | 10/1969 | Budnick | 260/502.4 |

FOREIGN PATENT DOCUMENTS 1026366  4/1966  United Kingdom .
1201984  8/1970  United Kingdom .

OTHER PUBLICATIONS

The Merck Index, 9th Ed., (1976), #3038.
Cram et al., "Organic Chemistry", 2nd Ed., (1965), pp. 265–266.

Primary Examiner—Anton H. Sutto
Attorney, Agent, or Firm—Beveridge, DeGrandi & Kline

[57] ABSTRACT

Fluorine-containing phosphonates and phosphonic acids are described. The method of preparation is a reaction of trialkylphosphites with dihalodifluoromethanes or a reaction of the salts of dialkylphosphites with halodifluoromethylphosphonates. The corresponding phosphonic acids are prepared by hydrolysis of the phosphonates.

1 Claim, No Drawings

METHOD FOR PREPARING FLUORINE-CONTAINING PHOSPHONATES

REFERENCE TO A RELATED APPLICATION

This application is a divisional application of our copending prior patent application Ser. No. 143,995 filed Apr. 28, 1980, now U.S. Pat. No. 4,330,486, the entire disclosure of which is incorporated and relied on herein by reference.

SUMMARY OF THE INVENTION

The present invention relates to fluorine-containing phosphonates and phosphonic acids and methods of preparing same. In particular, the fluorine-containing phosphonates are characterized by the formula:

wherein R is an alkyl group from 1 to 16 carbon atoms, preferably from 1 to 6 carbon atoms.

These compounds are diphosphonates and have been prepared by one of two methods.

Thus, the compounds of the invention may be prepared by the following sequence:

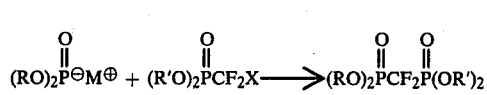

wherein M is an alkali metal, preferably Na or K, X is a halogen, preferably Cl, Br, or I As an alternative, the compounds may be prepared thusly

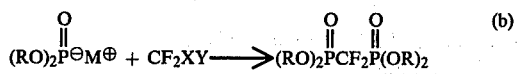

wherein X is halogen as before defined, and Y is halogen, preferably Cl Br and I; and M and R as defined above.

The corresponding acid is made by hydrolysis of the phosphonate compound by known means.

Typically, the reaction between $(BuO)_2P(O)CF_2Br$ and $(BuO)_2PONa$ in hexane was found to yield tetrabutyl difluoromethylene bis(phosphonate) (1) in 47% isolated yield. A 27% yield of the reduced dibutyl monophosphonate was also isolated. The spectral and analytical data of the bis (phosphonate) were entirely compatible with the structural assignment. (Bu is butyl)

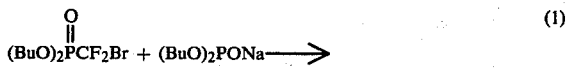

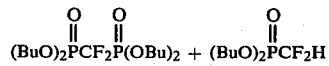

Similarly, the reaction between $(EtO)_2P(O)CF_2Br$ and sodium diethyl phosphite in hexane afforded tetraethyl difluoromethylene bis(phosphonate) (2) in 13% isolated yield. (Et is ethyl). The considerable difference in yields between (1) and (2) can probably be ascribed to the solubility differences of their corresponding sodium dialkyl phosphites. Sodium dibutyl phosphite is freely soluble in hexane, whereas sodium diethyl phosphite is much less soluble. No effort has been made to entirely optimize either of these reactions and high isolated yields are undoubtedly possible. The mechanism for these reactions can be viewed as abstraction of positive bromine from the initial phosphonate followed by recombination.

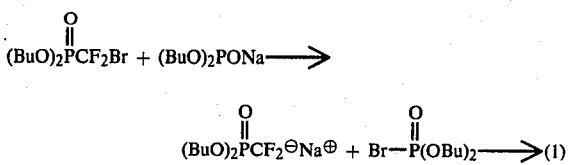

The mechanism is, however, more complex. The reaction between sodium dibutyl phosphite and $(EtO)_2P(O)CF_2Br$ afforded three bis(phosphonates) as observed in the $^{19}F$ nmr spectrum in a 1:2:1 ratio.

Generally, the reaction is carried out in an inert, hydrocarbon, non-protic solvent. This reduces the amount of reduction product formed in the reaction. Particularly good results were obtained using toluene.

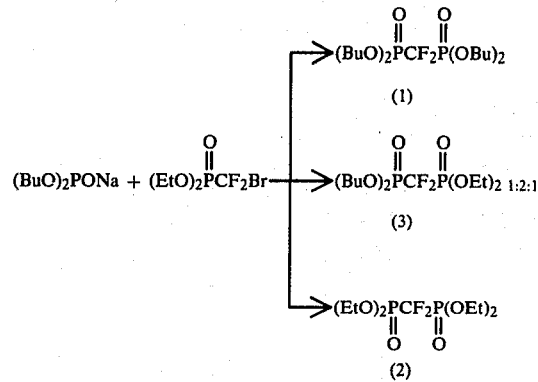

Two of these bis(phosphonates) were identified as (1) and (2) by enhancement of their respective signals in the $^{19}F$ nmr spectrum upon addition of authentic samples of each. The remaining triplet was assigned the mixed bis(phosphonate) structure (3). Fortunately, (2) was both considerably more water soluble and lower boiling than either (1) or (3) and was entirely removed in the workup of the reaction mixture. The unsymmetrical bis(phosphonate) (3) could not be separated entirely from (1). The $^{19}F$ nmr spectrum of the mixture showed two triplets: $\delta = 121.7$ J = 87 Hz (3) and $\delta = 121.4$ J = 87 Hz (1). The $^{31}P$ nmr spectrum showed only a triplet. The $^{1}H$ nmr spectrum clearly indicated the presence of an ethyl group. Finally, the $^{13}C$ nmr spectrum revealed all seven carbons for the alkyl groups of (3) as well as a (t,t) for the difluoromethyl ene carbon atom. The butyl carbons of (3) did, however, overlap with the butyl carbons of (1). A rationale for the observations of the three bis-(phosphonates) is shown in the equation below:

Mechanistic scheme for the reaction between (BuO)₂PONa and (EtO)₂P(O)CF₂Br

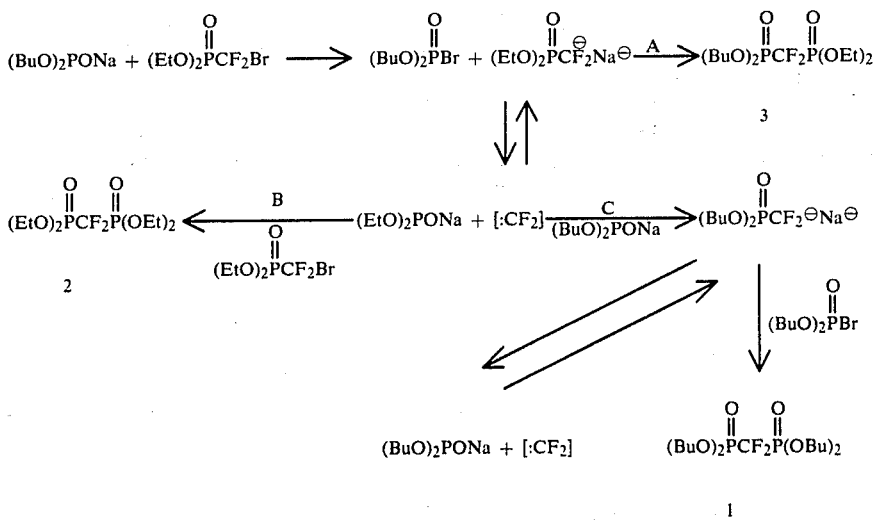

In path [A] the recombination of the phosphonate ylide and the acid bromide lead directly to the mixed phosphonate 3. If, instead of recombination, the ylide were to collapse to [:CF₂] and (EtO)₂PONa, two alternate pathways arise. In path [B], the (EtO)₂PONa can react directly with the precursor phosphonate to afford 2. In path [C], the [:CF₂] can be trapped by the (BuO)₂PONa to afford the dibutyl ylide which can then react further with the acid bromide to give 1.

An attempt to intercept an ylide intermediate in this reaction by carrying out the synthesis in the presence of trifluoroacetophenone failed, since sodium dibutyl phosphite was found to react readily with the ketone. The ¹⁹F nmr and ³¹P nmr spectral data suggest that the product of this reaction is the enol phosphate.

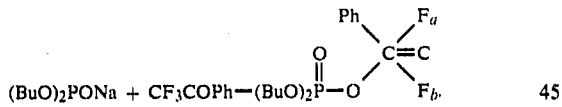

¹⁹F nmr: $F_a$: $\delta = 95.2(d,d)$ J(F,F)=55 Hz, J(F,P)=7.8 Hz; $F_b$: $\delta = 108.0(d,d)$ J(F,F)=55 Hz, J(F,P)=10.9 Hz
³¹P nmr: $\delta = 3.8(d,d)$ J(P,$F_a$)=5.6 Hz K(P,$F_b$)=9.4 Hz A more direct synthesis of the bis(phosphonates) would be from the reaction of (RO)₂PONa with CF₂Br₂. Sodium dibutyl phosphite reacted rapidly with the evaluation of heat with CF₂Br₂ in hexane. When an excess of CF₂Br₂ was employed both (BuO)₂P(O)CF₂Br and (1) were formed in a 1.4/1 ratio. The use of a 2:1 stoichiometry of phosphite anion to CF₂Br₂ again resulted in the formation of (BuO)₂P(O)CF₂Br and (1) in approximately the same ratio. Any inert, non-protic solvent may be used, although good results are obtained using toluene.

A more direct synthesis of the bis(phosponates) would be from the reaction of (RO)₂PONa with CF₂Br₂. Sodium dibutyl phosphite reacted rapidly with the evolution of heat with CF₂Br₂ in toluene. When an excess of CF₂Br₂ was employed both (BuO)₂P(O)CF₂Br and 1 were formed in a 1.4/1 ratio. The use of a 2:1 stoichiometry of phosphite anion to CF₂Br₂ again resulted in the formation of (BuO)₂P(O)CF₂Br and (1) in approximately the same ratio.

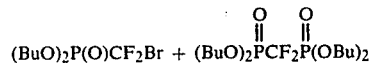

Apparently, a side reaction occurs which consumes (BuO)₂PONa in a non-productive step. The reaction between (BuO)₂PONa and

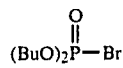

(formed in the initial stage of the reaction) would be a likely candidate.

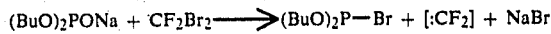

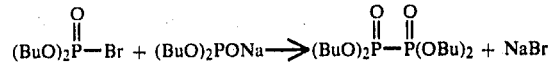

Generally, an inert hydrocarbon solvent such as hexane, a non-protic solvent, is used for the reaction. The reaction is exothermic and therefore no heating is required. For safety sake, it is desirable to cool the reactants and mix them slowly with agitation.

DETAILED DESCRIPTION OF THE INVENTION

The following examples serve to illustrate the invention:

EXAMPLE 1

To a solution of

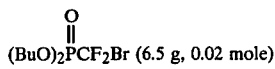(BuO)₂PCF₂Br (6.5 g, 0.02 mole)

in dry hexane (40 ml) cooled in an ice water bath was added slowly via syringe a solution of (BuO)₂PONa in hexane (25 ml, 0.02 mole). The (BuO)₂PONa solution was prepared by the reaction of Na metal (2 g, 0.087 mole) and (BuO)₂POH (16.8 g, 0.087 mole) in 80 ml dry hexane. This afforded a solution of concentration approximately 0.8M. After stirring for four hours, the mixture was poured into water (50 ml) and dried over anhydrous Na₂SO₄. The hexane was removed at room temperature via rotary evaporation at reduced pressure and the residue distilled to give 4.1 g (47%) of

(BuO)₂PCF₂P(OBu)₂

(bp 152–165/0.1 mm Hg) as well as 1.3 g (27%)

(BuO)₂PCF₂H(bp 170°/3.6 mm Hg). ¹⁹F nmr (BuO)₂PCF₂P(OBu)₂:

$\delta = 121.6$ (t) J=87 Hz; ¹H nmr: $\delta = 0.8$–1.1 (m,3H), $\delta = 1.1$–1.9 (m,4H), $\delta = 4.0$–4.4 (m, 2H); ³¹P nmr: $\delta = -3.7$ (t) J=86 Hz; ¹³C nmr: $\delta = 13.5$ (s) (CH₃—), $\delta = 18.6$ (s) (CH₃CH₂), $\delta = 32.5$ (3 peaks separated by 2.9 Hz—CH₂CH₂O), $\delta = 68.9$ (3 peaks separared by 3.7 and 2.9 Hz—CH₂O), $\delta = 116.3$ (t,t) J(C,P)=187 Hz J(C,F)=279 Hz (—CF₂—).

Analysis: Calculated for C₁₇H₃₆F₂O₆P₂: %C=46.79 %H=8.26;

Found: %C=46.79 %H=8.27.

EXAMPLE 2

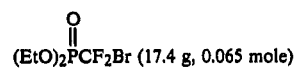(EtO)₂PCF₂P(OEt)₂

Diethyl phosphite (9.0 g, 0.065 mole) was syringed into a mixture of sodium metal (1.5 g, 0.065 mole) in dry hexane (50 ml). After the initial vigorous reaction had subsided, the solution was heated to reflux until the sodium metal had completely dissolved. The mixture was cooled in an ice bath and

(EtO)₂PCF₂Br (17.4 g, 0.065 mole)

added slowly via syringe. The reaction was rapid and the white solid dissolved and was replaced by a gray-green precipitate. After stirring for one hour at room temperature, water (50 ml) was added and three layers formed. The middle aqueous layer was separated and discarded; the top and bottom layers were combined and dried over anhydrous sodium sulfate. The hexane was removed by rotary evaporation at aspirator pressure and the residue distilled to yield 2.7 g (13%)

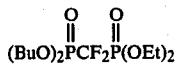(EtO)₂PCF₂P(OEt)₂

(bp 115°–118°/0.4 mm Hg) as well as a forerun (3 g) consisting of a 1:1 mixture of (EtO)₂

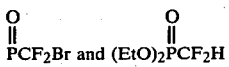PCF₂Br and (EtO)₂PCF₂H (bp 46.5°–47.5°/0.4 mm Hg). The ¹⁹F nmr spectrum of

(EtO)₂PCF₂P(OEt)₂:

$\delta = 122.0$ (t) J=87 Hz; ¹H nmr: $\delta = 1.40$ (t) J=7 Hz (CH₃); $\delta = 4.39$ (d,q) J (H,H)=7 Hz, J(H,P) $\delta = 3.8$ Hz (CH₂O); ³¹P nmr: $\delta = -3.5$ (t) J=86 Hz; ¹³C nmr: $\delta = 16.4$ (s) (CH₃—); $\delta = 65.3$ (d) J=2.9 Hz; $\delta = 116.2$ (t,t) J(C,P)=187 Hz, J(C,F)=279 Hz.

Analysis: Calculated for C₉H₂₀F₂O₆P₂: %C=33.33 %H=6.17;

Found: %C=33.41 %H=6.32.

EXAMPLE 3

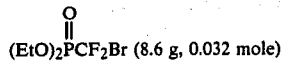(BuO)₂PCF₂P(OEt)₂

Dibutyl phosphite (6.26 g, 0.032 mole) was added to sodium metal (0.74 g, 0.032 mole) in dry hexane (30 ml) and the mixture stirred overnight under an inert atmosphere. After dissolution of the sodium, the solution was transferred to a 60 ml constant addition funnel and added slowly dropwise to an ice cold solution of

(EtO)₂PCF₂Br (8.6 g, 0.032 mole)

in hexane. A check of the ¹⁹F nmr spectrum of the solution after completion of the addition revealed that all of (EtO)₂PCF₂Br had been consumed and that three triplets were present at

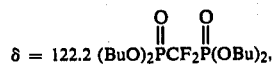$\delta = 122.2$ (BuO)₂PCF₂P(OBu)₂,

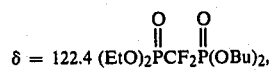$\delta = 122.4$ (EtO)₂PCF₂P(OBu)₂,

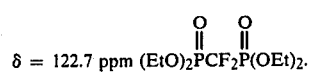$\delta = 122.7$ ppm (EtO)₂PCF₂P(OEt)₂.

Water (50 ml) was added to the reaction mixture and the organic layer was separated and washed again with water. The two aqueous layers were combined and examined by ¹⁹F nmr. The ¹⁹F nmr spectrum revealed that the aqueous layers contained

(EtO)$_2$PCF$_2$P(OEt)$_2$ as the only fluorine containing compound. The organic layer was dried over anhydrous MgSO$_4$, the hexane removed via rotary evaporation at aspirator pressure and the residue distilled to yield two fractions. The first contained (BuO)$_2$PCF$_2$P(OBu)$_2$ and the unsymmetrical bis (phosphonate)

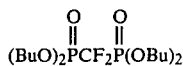
(EtO)$_2$PCF$_2$P(OBu)$_2$ in about a 3:1 ratio (bp 126°–136°/0.2 mm Hg). The second fraction contained the same products in a 1:2 ratio (bp 147–153/0.2 mm Hg); no

(EtO)$_2$PCF$_2$P(OEt)$_2$ was observed. $^1$H nmr: butyl protons of (BuO)$_2$PCF$_2$P(OBu)$_2$ and (EtO)$_2$PCF$_2$P(OBu)$_2$ overlap, 1 CH$_3$CH$_2$O (EtO)$_2$PCF$_2$P(OBu)$_2$:

$\delta = 1.38$ (t) J = 7 Hz; $^{19}$F nmr (EtO)$_2$PCF$_2$P(OBu)$_2$:

$\delta = 121.7$ (t) J = 87 Hz; $^{31}$P nmr: $\delta = -3.7$ (t) J = 86 Hz (overlap of (BuO)$_2$PCF$_2$P(OBu)$_2$ and (EtO)$_2$PCF$_2$P(OBu)$_2$; $^{13}$C nmr:

(butyl carbons of (BuO)$_2$PCF$_2$P(OBu)$_2$ and (EtO$_2$PCF$_2$P(OBu)$_2$ overlap: $\delta = 13.5$ (s), $\delta = 186$ (s), $\delta = 32.5$ (t) J = 3 Hz, $\delta = 68.9$ (t) J 3 Hz (butyl carbons); $\delta = 16.4$ (t) J = 3 Hz (CH$_3$CH$_2$O), $\delta = 65.4$ (d) J = 3 Hz (CH$_3$CH$_2$O); $\delta = 116.2$ (t,t) J (C,P) = 188 Hz, J (C, F) = 279 Hz. The assignments of the butyl carbons and the ethyl carbons was made by comparison to the spectral data of (BuO)$_2$PCF$_2$P(OBu)$_2$ and (EtO)$_2$PCF$_2$(OEt)$_2$ respectively.

Using the same reaction procedure as set forth in the examples it is possible to make compounds of the formula (RO)$_2$PCF$_2$P(OR')$_2$ wherein R is 1 to 12 carbons, preferably 1 to 6.

These compounds can be used in the following ways: as detergents and as chelating agents for ions.

We claim:

1. A method of making a compound having the formula (RO)$_2$PCF$_2$P(OR')$_2$ comprising reacting a compound of the formula (RO)$_2$P$^{\ominus}$M$^{\oplus}$
    ‖
    O with a compound of the formula:

CF$_2$XY wherein R and R' are alkyl from 1 to 16 caron atoms, X and Y are the same or different halogen and M is alkali metal, wherein the halogen is selected from the group consisting of chlorine, bromine and iodine.

* * * * *